United States Patent
Fleury et al.

(10) Patent No.: US 9,737,393 B2
(45) Date of Patent: Aug. 22, 2017

(54) TRACHEAL IMPLANT

(71) Applicant: BOSTON SCIENTIFIC SCIMED, INC., Maple Grove, MN (US)

(72) Inventors: Sean Fleury, Brighton, MA (US); Jason Weiner, Grafton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 22 days.

(21) Appl. No.: 14/946,125

(22) Filed: Nov. 19, 2015

(65) Prior Publication Data

US 2016/0143724 A1 May 26, 2016

Related U.S. Application Data

(60) Provisional application No. 62/082,411, filed on Nov. 20, 2014.

(51) Int. Cl.
*A61F 2/20* (2006.01)
*A61F 2/04* (2013.01)
*A61F 2/07* (2013.01)

(52) U.S. Cl.
CPC .......... *A61F 2/04* (2013.01); *A61F 2002/046* (2013.01); *A61F 2002/072* (2013.01); *A61F 2210/0057* (2013.01); *A61F 2230/0008* (2013.01); *A61F 2230/0034* (2013.01); *A61F 2230/0069* (2013.01)

(58) Field of Classification Search
CPC .................................. A61F 2/203; A61F 2/20
USPC ............................................................ 623/9
See application file for complete search history.

(56) References Cited

U.S. PATENT DOCUMENTS

| 5,236,447 | A | 8/1993 | Kubo et al. |
| 5,258,027 | A | 11/1993 | Berghaus |
| 6,547,825 | B1 | 4/2003 | Shimizu et al. |
| 7,001,420 | B2 * | 2/2006 | Speck ............... A61M 25/005 604/103.09 |
| 8,709,080 | B2 | 4/2014 | Marten et al. |
| 8,968,401 | B2 * | 3/2015 | Seifalian ............... A61F 2/04 623/9 |
| 2006/0069425 | A1 * | 3/2006 | Hillis .................. A61F 2/82 623/1.16 |
| 2007/0219642 | A1 * | 9/2007 | Richter ................ A61F 2/91 623/23.7 |
| 2008/0243230 | A1 * | 10/2008 | Lootz .................. A61F 2/91 623/1.15 |
| 2009/0312834 | A1 * | 12/2009 | Wood .................. A61F 2/90 623/1.44 |

(Continued)

FOREIGN PATENT DOCUMENTS

WO      WO 93/00869 A1      1/1993

OTHER PUBLICATIONS

International Search Report and Written Opinion dated Mar. 2, 2016, in corresponding International Application No. PCT/US2015/061544.

*Primary Examiner* — Suzette J Gherbi
(74) *Attorney, Agent, or Firm* — Bookoff McAndrews, PLLC

(57) ABSTRACT

An implant device may include a body of a first material and defining a lumen and at least two arcuate rings of a second material embedded within the body. In one embodiment, the second material does not connect a first ring of the at least two arcuate rings to an adjacent second ring of the at least two arcuate rings.

20 Claims, 3 Drawing Sheets

(56) References Cited

U.S. PATENT DOCUMENTS

| | | | |
|---|---|---|---|
| 2013/0066438 A1 | 3/2013 | Seifalian | |
| 2014/0228930 A1* | 8/2014 | Papp | A61F 2/915 |
| | | | 623/1.11 |
| 2015/0230918 A1* | 8/2015 | Detamore | A61F 2/20 |
| | | | 623/9 |
| 2015/0374522 A1* | 12/2015 | Wood | A61F 2/95 |
| | | | 623/1.12 |
| 2016/0022449 A1* | 1/2016 | Lim | A61F 2/04 |
| | | | 623/9 |
| 2016/0051385 A1* | 2/2016 | Hollister | A61F 2/848 |
| | | | 623/1.28 |
| 2016/0106536 A1* | 4/2016 | Chui | A61F 2/20 |
| | | | 623/9 |
| 2016/0143729 A1* | 5/2016 | Matheny | A61F 2/203 |
| | | | 623/9 |

* cited by examiner

TRACHEAL IMPLANT

CROSS-REFERENCE TO RELATED APPLICATION

This application claims the benefit of priority under 35 U.S.C. §119 to U.S. Provisional Patent Application No. 62/082,411, filed Nov. 20, 2014, the entirety of which is incorporated herein by reference.

TECHNICAL FIELD

Embodiments of the present disclosure relate generally to medical devices for repairing passageways within a patient, particularly respiratory system passageways such as the trachea or bronchi.

BACKGROUND

Currently, it is difficult to repair a patient's trachea, main bronchus, or other respiratory system passageways (i.e., airways) after removal of a portion of the airway. The removed portion of the airway may be too large to reconnect the ends on either side of the resection, and current implant options may be too expensive or ineffective.

One option for reconnecting two ends of an airway is to grow a replacement implant on a scaffold using the patient's cells. However, it may take days or weeks for the cells to fully develop on the scaffold, which can be costly. Furthermore, multiple surgical procedures may be required to first harvest cells from the patient and then implant the new portion of the trachea or other airway. The airway replacement portions grown on a scaffold may also fail to structurally and functionally mimic a human airway. For example, replacement tracheas grown on a scaffold may not account for the differences between cartilage rings and smooth muscle tissue in a real trachea.

Another current option for repairing a patient's airway is to replace a removed portion with tissue from another species. However, using tissue from another living (or previously living) source carries risks. The implanted tissue may transfer an infection to the patient, or the patient may reject the foreign tissue.

SUMMARY

Embodiments of the present disclosure relate to, among other things, implant devices and methods for implanting an implant device in a passageway of a patient. Each of the embodiments disclosed herein may include one or more of the features described in connection with any of the other disclosed embodiments.

In one example, an implant device may include a body of a first material and defining a lumen and at least two arcuate rings of a second material embedded within the body. In one embodiment, only the first material connects a first ring of the at least two arcuate rings to an adjacent second ring of the at least two arcuate rings.

The implant device may include one or more of the following features: additionally or alternatively the body may include an outer planar surface; additionally or alternatively the planar surface may be configured to be movable from the planar configuration to a curved configuration; additionally or alternatively at least one arcuate ring may be C-shaped, and the planar surface may connect a first end of the C-shaped ring to a second end of the C-shaped ring; additionally or alternatively the body may be elongated along a longitudinal axis; additionally or alternatively the first material may be a liquid silicone rubber and the second material may be a different liquid silicone rubber; additionally or alternatively the implant device may include between 10 and 25 rings, the second material may not connect any two adjacent rings, and only the first material may be between any two adjacent rings; additionally or alternatively the implant device may further include a mesh at least partially embedded within a first end of the body; additionally or alternatively the implant device may include at least one suture loop protruding from a first end of the body; additionally or alternatively the implant device may be configured to return to an original length after the original length of the implant device has been extended by 20%; additionally or alternatively an axial extension force of the implant device at a 20% extension may be between 1.1 N and 2.7 N; additionally or alternatively each of the at least two arcuate rings may have a tensile strength between 2 Mpa and 15 Mpa, a flexural modulus between 8.27 MPa and 27.58 MPa, and a durometer between 75 and 90 on a Shore A scale; additionally or alternatively each of the at least two arcuate rings may be entirely embedded within the first material; additionally or alternatively the implant device may be configured to be implanted in a human respiratory system passageway; and additionally or alternatively a cross-sectional width of each of the at least two arcuate rings may be between 3.5 mm and 4.5 mm.

In another example, an implant device may include a body of a first material and defining a lumen and at least one arcuate ring of a second material embedded within the body. The body may include a substantially planar surface.

The implant device may include one or more of the following features: additionally or alternatively the implant device may be configured to return to an original length after the original length of the implant device has been extended by 20%; additionally or alternatively an axial extension force of the implant device at a 20% extension may be between 1.1 N and 2.7 N; additionally or alternatively the at least one arcuate ring may have a tensile strength between 2 Mpa and 15 Mpa, a flexural modulus between 8.27 MPa and 27.58 MPa, and a durometer between 75 and 90 on a Shore A scale; additionally or alternatively the at least one arcuate ring may be entirely embedded within the first material; additionally or alternatively the implant device may be configured to be implanted in a human respiratory system passageway; additionally or alternatively the implant device may include between 10 and 25 rings, and each ring may be connected to at least one adjacent ring by only the first material; and, additionally or alternatively, a cross-sectional width of the at least one arcuate ring may be between 3.5 mm and 4.5 mm.

In a further example, a method for implanting an implant device may include implanting an implant device in a respiratory passageway of a patient. The implant device may include an elongated body of a first material and defining a lumen and at least one arcuate ring of a second material embedded within the elongated body.

The method may include one or more of the following features: additionally or alternatively the step of implanting the implant device may include suturing at least one of suture loops and a mesh to a natural trachea; additionally or alternatively the second material may not connect the at least one arcuate ring to at least one adjacent arcuate ring; and, additionally or alternatively, the elongated body may include a substantially planar surface.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description serve to explain the principles of the disclosure.

DETAILED DESCRIPTION

Overview

Embodiments of the present disclosure may include medical devices for implanting in a patient, particularly within the patient's respiratory system. The implant devices disclosed herein may be used to support or replace all or portions of a patient's trachea, primary bronchi, secondary bronchi, tertiary bronchi, or any other suitable passageway within the patient.

Exemplary Embodiments

Figure 1:
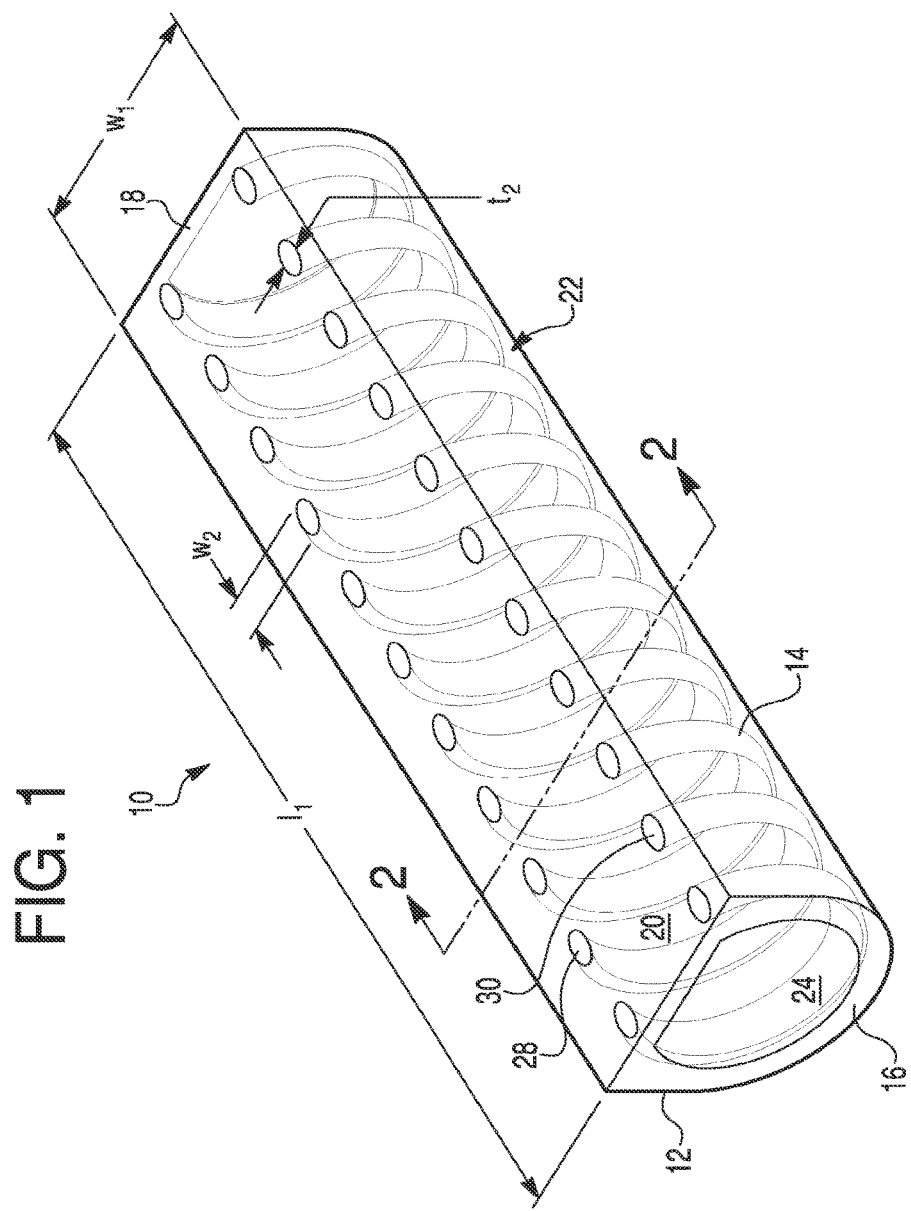
FIG. 1 illustrates a perspective view of an implant device, according to an exemplary embodiment.

Referring to FIG. 1, an implant device 10 may include a main body 12 of a first material and rings 14 of a second material. The rings 14 may be embedded within the first material of the main body 12. The first material of the main body 12 may have properties that are similar to properties of muscle and other tissue in a natural body passageway. Similarly, the second material of the rings 14 may have properties that are similar to properties of cartilage in a natural body passageway, such as a trachea or bronchus.

Figure 2:
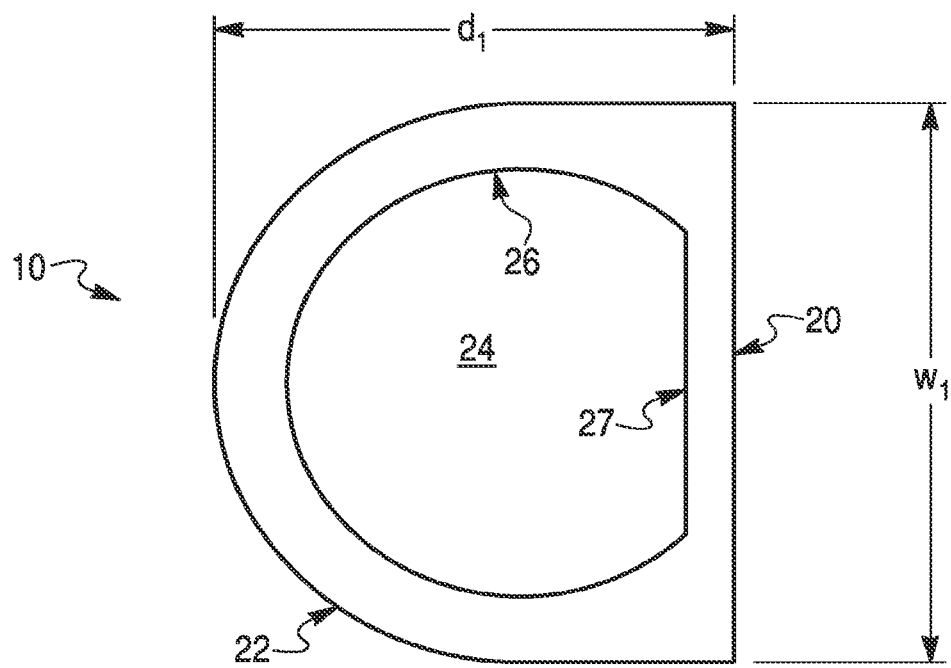
FIG. 2 illustrates a cross-sectional view of an implant device, according to an exemplary embodiment.

Referring to FIGS. 1 and 2, the implant device 10 may have a first end 16, a second end 18, a length "$l_1$," a width "$w_1$," and a depth "$d_1$." The main body 12 may be substantially elongated along its longitudinal axis, with a lumen 24 extending from the first end 16 to the second end 18. The main body 12 may have an outer curved surface 22 and an outer planar or substantially planar surface 20. The main body 12 also may have an inner curved surface 26 and an inner planar or substantially planar surface 27 surrounding the lumen 24. In other embodiments, the inner surfaces 26 and 27 of the lumen 24 may form a circular cross section, or any other suitable shape.

In one embodiment, the implant device 10 may have similar dimensions to the portion of the natural passageway that it is replacing. For example, if the implant device 10 will be used to replace an entire trachea, the implant device 10 may have similar dimensions to a natural trachea.

In one embodiment, the length $l_1$ of the implant device 10 may be between 1-15 cm. If being used to replace an entire trachea, for example, the length $l_1$ may be between 11-13 cm. In another embodiment, if being used to replace a shorter portion of a passageway, for example, the length $l_1$ may be 2-4 cm. The length $l_1$ of the implant device 10, however, may fall within any range or combination of ranges or may be any specific length, and may be customizable depending on the portion of the passageway being replaced.

Some portions of the implant device 10 may be formed only of the first material of the main body 12 (e.g., between the rings 14 or along planar surface 20). The portions formed only of the first material may have a first thickness. In some embodiments, the first thickness may be between 1-2.5 mm. In one embodiment, the first thickness may be 1.95 mm. The portions of the implant device 10 that include the rings 14 may have a second thickness. In some embodiments, the second thickness may be between 2-3 mm. In one embodiment, the second thickness may be about 2.37 mm. The first and second thicknesses can be customized depending on the patient's needs and the desired implant device properties. In one embodiment, the first and second thicknesses may be equal.

The width $w_1$ and depth $d_1$ of the implant device 10 may also be customizable depending on the patient. For example, the width $w_1$ of the implant device 10 may be between 10 mm and 25 mm and the depth $d_1$ may be between 8 mm and 20 mm, depending on the size of the patient. In one embodiment, the inner curved surface 26 and outer curved surface 22 each may be portions of circles (e.g., FIG. 3A). In other embodiments, the inner curved surface 26 may be a portion of a circle while the outer curved surface 22 may be substantially U-shaped (e.g., FIG. 2). Portions of a U-shaped curved surface may be partially defined by a circle having a certain diameter. The width $w_1$ of the implant device 10 (i.e., the length of planar surface 20) may be related to the size of a circle that would form all or parts of the inner curved surface 26 or the outer curved surface 22.

In one embodiment, width $w_1$ of the implant device 10 may be calculated by taking a percentage of the diameter of the circle that would create part or all of outer curved surface 22. For example, in one embodiment, the width $w_1$ of the implant device may be 45-65% of the diameter of the circle that would form part or all of outer curved surface 22. Similarly, the length of the inner planar surface 27 may be calculated by taking a percentage of the diameter of the circle that would form part or all of inner curved surface 26. In one embodiment, the length of the inner planar surface 27 may be 45-65% of the diameter of the circle that would form inner surface 26. In some embodiments, the width $w_1$ of the implant device or the length of inner surface 27 may be about 55% of the diameter of a circle that would create part or all of curved surface 22 or curved surface 26.

In one embodiment, the implant device 10 may be manufactured such that the center of the circle that would form the inner curved surface 26 is a certain distance away from the inner planar surface 27. In some embodiments, the distance from the center of the circle to the inner planar surface 27 may be between 30-50% of the diameter of the circle that would form inner curved surface 26. In one embodiment, the distance from the center of the circle to the inner planar surface 27 may be about 38.7% of the diameter of the circle.

The main walls of the device 10 (i.e., along planar surface 20 and outer curved surface 22) may be solid and have no apertures. In this embodiment, fluid may not be able to flow through the walls of the device 10, and tissue may not be able to grow through the walls of the device 10. In other embodiments, apertures may be included in the walls of the device 10 to allow fluid transfer or tissue growth.

The implant device 10, comprising the first material of the main body 12 and the second material of the rings 14, may have an axial extension force that is similar to a natural passageway. The axial extension force may be a measure of the force exerted by each end of the implant device 10 when extended along its longitudinal axis. In one embodiment, the axial extension force of the implant device 10, measured when the implant device 10 has been extended by a certain percentage, is similar to the axial extension force of a natural human trachea that has been extended by the same percentage. For example, if a natural human trachea has an axial extension force of x at 20% extension, the implant device 10 may also have an axial extension force of x at 20% extension. Said another way, the force required to extend the length of the implant device 10 by 20% may be about the same as the force required to extend the length of a natural trachea by 20%. In some embodiments, the axial extension force of the implant device 10 at 20% elongation is between 1.1 N and 2.7 N. In other embodiments, the axial extension force of the implant device 10 at 20% elongation is between 1.55 N and 2.0 N. In one embodiment, the axial extension force of the implant device 10 at 20% elongation is 1.65 N.

The first material of the main body 12 may be selected such that the main body 12 is biocompatible and has desired properties. In one embodiment, the first material of the main body 12 may be selected such that the implant device 10, with the embedded rings 14, will have a desired axial extension force at a certain extension. For example, the axial extension force may be measured at 20% elongation because the maximum extension that a human trachea experiences during coughing, deep breathing, or sneezing is about 20%. However, the axial extension force may be measured at other elongations, such as 5%, 10%, 15%, 25%, or any other percentage elongation. The first material of the main body 12 may be a liquid silicone rubber. Examples of liquid silicone rubbers that may be suitable for the main body 12 include Med-4086 and Med-4901, although other suitable materials may also be used.

The substantially planar surface 20 of the implant device 10 may have properties that allow it to function similarly to the substantially planar portion of a natural passageway, such as a natural trachea. For example, when implanted in a patient, the implant device 10 may be positioned parallel to the esophagus such that the planar surface 20 contacts the esophagus. The patient's esophagus expands when the patient swallows food. Thus, the planar surface 20 may be flexible enough to allow it to be pushed inwards, towards the interior of lumen 24, during expansion of the esophagus. When the planar surface 20 is pushed inwards, a cross section of the implant device 10 may be crescent-shaped. The substantially planar surface 20 therefore may be configured to be movable from its original substantially planar configuration to a substantially curved configuration. Similarly, when implanted, forces from the interior of lumen 24 may push outward, causing the substantially planar surface 20 to bulge outward into a substantially curved configuration. In this manner, the properties of the planar surface 20 may help the implant device 10 function as a natural trachea during eating and other activities.

The implant device 10 may include a plurality of rings 14. The number of rings may depend on the length of the passageway to be replaced or repaired. In some embodiments, the implant device 10 may include only one or two rings. In other embodiments, the implant device 10 may include 1-5, 6-10, 11-15, 16-20, 21-25, or 25-30 rings, or any other range, combination of ranges, or specific number of rings that would provide the necessary support for the implant device 10.

Each ring 14 may be arcuate with a first end 28 and a second end 30. In one embodiment, the rings 14 are substantially C-shaped. The spacing between the first ends 28 and the second ends 30 of the rings 14 may allow the implant device 10 to function like the natural passageway that it replaced. For example, in a natural trachea, coughing causes the soft tissue portion (i.e., where there are no cartilage rings) to move inwards such that a cross section of the natural trachea appears crescent-shaped. Similarly, when the implant device 10 is implanted in a patient, the planar surface 20 between the first ends 28 and the second ends 30 of the rings 14 may move into the lumen 24 when the patient coughs. Similar to a natural trachea, inward movement of the planar surface 20 may increase the velocity of air moving out of the patient, which may aid in removal of irritants from the patient's body. In this manner, the spacing between first ends 28 and second ends 30 of the rings 14 may help the implant device 10 function as a natural trachea during coughing, sneezing, and other respiratory system actions.

One longitudinal edge of the planar surface 20 of the main body 12 may connect a plurality of ring first ends 28, and the opposite longitudinal edge of the planar surface 20 may connect a plurality of ring second ends 30. Accordingly, in this embodiment, a continuous portion of the planar surface 20 extending from the first end 16 to the second end 18 of the implant device 10 may include only the first material of the main body 12. Thus, this continuous longitudinal portion of the planar surface 20 may not include the second material of the rings 14.

In one embodiment, the rings 14 are entirely embedded in the first material such that the first material surrounds all sides of the rings 14. In other embodiments, the rings 14 may be partially embedded in the first material of the main body 12 such that only a portion of the rings 14 are surrounded by the first material of the main body 12. When only partially embedded, portions of the rings 14 may not be covered by the first material of the main body 12 and may be exposed on either the outer surface 22 or the inner surface 26.

When embedded within the first material of the main body 12, the rings 14 may be connected to adjacent rings 14 by the first material but may not be connected to adjacent rings 14 by the second material. In the embodiment in which the rings 14 are connected to adjacent rings by the first material but not by the second material, the rings 14 may provide support for the implant device while allowing the implant device 10 to extend and contract along its longitudinal axis. When used to replace a portion of the patient's trachea, for example, allowing extension and contraction of the implant device 10 may allow the lungs to naturally drop and rise within the patient's thoracic cavity during respiratory system activities such as breathing, coughing, and sneezing. In this manner, the rings 14 not being connected to adjacent rings 14 by the second material may allow the implant device 10 to extend and contract similarly to a natural trachea. In other embodiments, some rings 14 may be connected to adjacent rings 14 by the second material.

The rings 14 may have a width "$w_2$" and a thickness "$t_2$." The rings 14 may further have a length "$l_2$" (not shown), which is the distance along the rings 14 from their first ends 28 to their second ends 30. The rings 14 may be thicker in the middle and decrease in thickness towards the edges of rings 14. In some embodiments, the width $w_2$ may be between 3.5-4.5 mm. In one embodiment, the width $w_2$ may be 4 mm. In some embodiments, the thickness $t_2$ of the rings 14 may be between 0.75-2 mm. In one embodiment, the thickness $t_2$ of the rings 14 may be about 1 mm. In some embodiments, the length $l_2$ may be between 2 mm-4 mm. In one embodiment, the length $l_2$ may be 4.5 mm. The rings 14 also may be spaced apart from adjacent rings. In some embodiments, there may be between 0-2 mm between adjacent rings 14. In one embodiment, there may be about 1.5 mm between adjacent rings 14. Any of the dimensions of rings 14 and the spacing between adjacent rings 14 may be customizable depending on the patient and the desired properties of the implant device 10.

In one embodiment, the rings 14 have properties that are similar to the properties of natural cartilage. The properties may be tensile strength, flexural modulus, and durometer, although other properties may be relied on to manufacture the rings 14 to have properties similar to those of natural cartilage. In some embodiments, the tensile strength of the rings 14, measured when the rings 14 are in a flattened configuration, may be between 2-15 MPa. In other embodiments, the tensile strength of the rings 14 may be between 8-10 MPa. In yet another embodiment, the tensile strength of the rings 14 may be about 8.6 MPa.

A three-point bend test may be used to measure the flexural modulus of the rings 14. In some embodiments, the flexural modulus of the rings 14 may be between 1200-4000 psi (8.27-27.58 MPa). In other embodiments, the flexural modulus of the rings 14 may be between 2000-3000 psi (13.79-20.68 MPa). In yet another embodiment, the flexural modulus may be about 2323 psi (16.02 MPa).

The durometer of the rings 14 may be between 75-90 on the Shore A scale. In some embodiments, the durometer of the rings 14 may be between 78-83 on the Shore A scale. In yet another embodiment, the rings 14 may have a durometer of about 79.4 on the Shore A scale. The properties of the rings 14, including tensile strength, flexural modulus, and durometer, may be customized to meet the needs of a particular patient.

The rings 14 having desired properties may increase the effectiveness of the implant device 10. For example, if the implant device 10 is used to replace a portion of a patient's trachea, the rings 14 may help prevent the implant device 10 from collapsing under the pressure exerted on the implant device 10 when the patient coughs, breathes deeply, or sneezes.

The second material of the rings 14 may be selected such that the rings 14 have certain desired properties. In one embodiment, the second material of the rings 14 may be selected such that the rings 14 have a desired tensile strength, flexural modulus, and durometer. In one embodiment, the second material may be a liquid silicone rubber. Some examples of liquid silicone rubber suitable for the rings 14 include Med-4880 silicone, Wacker LR 3003/80, and Dow 7-4870.

In some embodiments, the main body 12 may include embedded second material portions that are not shaped like rings 14. For example, the second material portions could be formed into substantially square, circular, rectangular, or irregular shapes. In one embodiment, the second material portions may be shaped similarly to cartilaginous areas in natural respiratory system passageways.

Figure 3A:
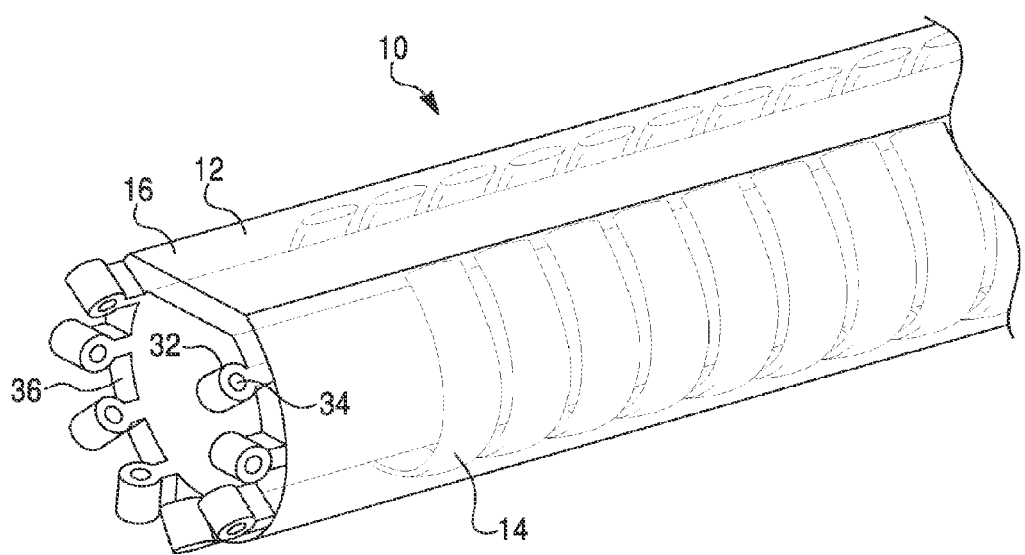
FIG. 3A illustrates a first exemplary embodiment of an attachment portion of an implant device.

Referring to FIG. 3A, a first embodiment of an attachment portion of an implant device 10 may include suture loops 32. The suture loops 32 may include an opening 34, which can be used to thread a suture. The suture loops 32 may be attached to a first end surface 36 of the implant device 10. Sutures may be used to attach the first end 16 of the implant device 10 to a cut end of a passageway. In one embodiment, the second end 18 of the implant device 10 also includes suture loops 32 to allow sutures to attach the second end 18 of the implant device 10 to a second cut end of a passageway. The suture loops 32 may be made of the same material as the main body 12. In an alternative embodiment, the suture loops 32 are made of a different material than the main body 12.

Figure 3B:
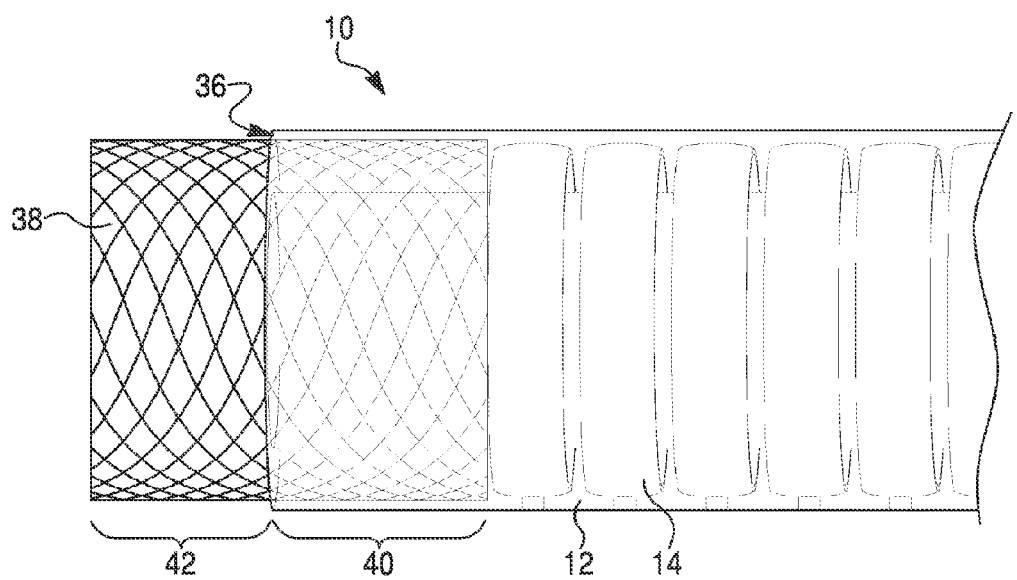
FIG. 3B illustrates a second exemplary embodiment of an attachment portion of an implant device.

Referring to FIG. 3B, a second embodiment of an attachment portion of an implant device 10 may include a mesh 38. A first portion 40 of the mesh 38 may be embedded in the main body 12 of the implant device 10. A second portion 42 of the mesh 38 may extend past the first end surface 36 of the implant device 10. Sutures may be threaded through openings in the second portion 42 to attach the first end 16 of the implant device 10 to a cut end of a natural passageway. The second end 18 of the implant device 10 may also include a mesh 38 and may be sutured to a second cut end of a natural passageway.

In alternative embodiments, one end of the implant device 10 may include suture loops 32 while the other end includes a mesh 38. The sutures used in connection with either suture loops 32 or mesh 38 may be biodegradable. Furthermore, the ends of the implant device 10 may include any other structures or features known in the art to enable the ends of the implant device 10 to be connected to natural portions of a passageway.

The implant devices 10 described herein may be made using a two-stage molding process. Examples of suitable molding processes may include cast molding and injection molding. In one stage of the molding process, the second material may be placed into a mold to form the rings 14. In another stage, the rings 14 may be placed into another mold, and the rings 14 may be coated by the first material to form the main body 12. Embedding the rings 14 within the first material of the main body 12 may simplify the manufacturing process of the implant device 10 because when using the embedding process, it may be unnecessary to attach the rings 14 to the main body 12 using an additional material, adhesive, or attachment mechanism.

The implant device 10 may be used to replace a portion of a patient's trachea, primary bronchi, secondary/tertiary bronchi, or any other suitable passageways within the body. The natural passageway portion may require replacement due to injury, cancer, or other abnormality. Once the natural passageway portion has been removed, the remaining natural passageway may have a first cut end and a second cut end. During implantation, the first end 16 of the implant device 10 may be connected to the first cut end of the remaining natural passageway. Similarly, the second end 18 of the implant device 10 may be connected to the second cut end of the remaining natural passageway. Sutures may be used to secure the implant device 10 to the remaining natural passageway via attachment portions, such as suture loops 32 or mesh 38. Over time, natural tissue may grow around the attachment portions of the implant device 10, securing the device in place.

Although the implant device 10 is well-suited to replace all or portions of a patient's trachea or bronchi, the implant device 10 alternatively can be used to replace other portions of natural passageways. For example, other passageways that include cartilage for support may be suitable candidates for receiving embodiments of the implant device 10.

In some embodiments, the implant device 10 may be used as a model of a natural passageway (e.g., the trachea) to test stents or other devices to be implanted in a patient. In still further embodiments, the implant device 10 may itself be used as a stent and may be implanted within a natural passageway to provide structural support.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. An implant device, comprising:
   a body of a first material and defining a lumen; and
   at least two arcuate rings of a second material embedded within the body, wherein a cross-sectional width of at least one arcuate ring of the at least two arcuate rings is from 3.5 mm to 4.5 mm;
   wherein the second material does not connect a first ring of the at least two arcuate rings to an adjacent second ring of the at least two arcuate rings.

2. The implant device of claim 1, wherein the body includes an outer substantially planar surface.

3. The implant device of claim 2, wherein the substantially planar surface is configured to be movable from a substantially planar configuration to a substantially curved configuration.

4. The implant device of claim 1, wherein the first material is a liquid silicone rubber and the second material is a different liquid silicone rubber.

5. The implant device of claim 1, wherein the implant device includes 10 to 25 rings, the second material does not connect any two adjacent rings, and only the first material is between any two adjacent rings.

6. The implant device of claim 1, wherein at least one arcuate ring is C-shaped, and wherein a substantially planar surface connects a first end of the C-shaped ring to a second end of the C-shaped ring.

7. The implant device of claim 1, further comprising a mesh at least partially embedded within a first end of the body.

8. The implant device of claim 1, further comprising at least one suture loop protruding from a first end of body.

9. An implant device, comprising:
   a body of a first material and defining a lumen; and
   at least one arcuate ring of a second material embedded within the body, wherein the at least one arcuate ring has a tensile strength from 2 Mpa to 15 Mpa, a flexural modulus from 8.27 MPa to 27.58 MPa, and a durometer from 75 to 90 on a Shore A scale;
   wherein the body includes a substantially planar surface.

10. The implant device of claim 9, wherein the implant device is configured to return to an original length after the original length of the implant device has been extended by 20%.

11. The implant device of claim 9, wherein an axial extension force of the implant device at a 20% extension is from 1.1 N to 2.7 N.

12. The implant device of claim 9, wherein the at least one arcuate ring is entirely embedded within the first material.

13. The implant device of claim 9, wherein the implant device is configured to be implanted in a human respiratory system passageway.

14. The implant device of claim 9, wherein the implant device includes 10 to 25 rings, and each ring is connected to at least one adjacent ring by only the first material.

15. The implant device of claim 9, wherein a cross-sectional width of the at least one arcuate ring is from 3.5 mm to 4.5 mm.

16. A method for implanting an implant device, comprising:
   implanting an implant device in a respiratory passageway of a patient such that the implant device is coupled to or replaces a natural trachea, wherein the implant device includes:
      a body of a first material and defining a lumen; and
      at least one arcuate ring of a second material embedded within the body.

17. The method of claim 16, wherein the step of implanting the implant device includes suturing at least one of a suture loop and a mesh to the natural trachea.

18. The method of claim 16, wherein the second material does not connect the at least one arcuate ring to at least one adjacent arcuate ring.

19. The method of claim 16, wherein the body includes a substantially planar surface.

20. The implant device of claim 1, wherein at least one arcuate ring of the at least two arcuate rings has a tensile strength from 2 Mpa to 15 Mpa, a flexural modulus from 8.27 MPa to 27.58 MPa, and a durometer from 75 to 90 on a Shore A scale.

* * * * *